United States Patent
Voeller et al.

(10) Patent No.: US 8,105,246 B2
(45) Date of Patent: Jan. 31, 2012

(54) ELONGATE MEDICAL DEVICE HAVING ENHANCED TORQUE AND METHODS THEREOF

(75) Inventors: Virgil F. Voeller, St. Louis Park, MN (US); Clay W. Northrop, Salt Lake City, UT (US); Justin M. Crank, Maple Grove, MN (US); Ted W. Layman, Park City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 920 days.

(21) Appl. No.: 11/833,684

(22) Filed: Aug. 3, 2007

(65) Prior Publication Data

US 2009/0036834 A1    Feb. 5, 2009

(51) Int. Cl.
*A61B 5/00* (2006.01)
*A61M 25/00* (2006.01)

(52) U.S. Cl. ........ 600/585; 604/523; 604/524; 604/525; 604/526

(58) Field of Classification Search .......... 600/585; 604/523–526
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |

(Continued)

FOREIGN PATENT DOCUMENTS

AU    723040    12/1997

(Continued)

OTHER PUBLICATIONS

"Mechanical Design and Systems Handbook", H.A. Rothbart, 1964, p. 33-13 (one sheet).

*Primary Examiner* — Max Hindenburg
*Assistant Examiner* — Sean Dougherty
(74) *Attorney, Agent, or Firm* — Seager, Tufte & Wickhem, LLC

(57) ABSTRACT

An elongate medical device such as a guidewire, that may comprise a first elongate member having a proximal end, a distal end and a lumen there between, a second elongate member having a proximal end and a distal end, the second elongate member at least partially disposed in the first elongate member, a first connection between first elongate member and the second elongate member at the proximal end of the first elongate member, a second connection between the first elongate member and the second elongate member at the distal end of the first elongate member, and a third connection between the first elongate member and the second elongate member, the third connection disposed at a point between the first connection and the second connection, wherein the third connection is substantially at a location selected by the Method for Enhancing the Ratio of Torsional Stiffness to Transverse Flexibility.

46 Claims, 6 Drawing Sheets

U.S. PATENT DOCUMENTS

| | | |
|---|---|---|
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Willson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gambale |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |

| Patent | Kind | Date | Inventor |
|---|---|---|---|
| 5,601,539 | A | 2/1997 | Corso, Jr. |
| 5,605,162 | A | 2/1997 | Mirzaee et al. |
| 5,622,184 | A | 4/1997 | Ashby et al. |
| 5,630,806 | A | 5/1997 | Inagaki et al. |
| 5,637,089 | A | 6/1997 | Abrams et al. |
| 5,656,011 | A | 8/1997 | Uihlein et al. |
| 5,658,264 | A | 8/1997 | Samson et al. |
| 5,666,968 | A | 9/1997 | Imran et al. |
| 5,666,969 | A | 9/1997 | Urick et al. |
| 5,669,926 | A | 9/1997 | Aust et al. |
| 5,676,659 | A | 10/1997 | McGurk |
| 5,676,697 | A | 10/1997 | McDonald |
| 5,682,894 | A | 11/1997 | Orr et al. |
| 5,690,120 | A | 11/1997 | Jacobsen et al. |
| 5,720,300 | A | 2/1998 | Fagan et al. |
| 5,722,609 | A | 3/1998 | Murakami |
| 5,728,063 | A | 3/1998 | Preissman et al. |
| 5,741,429 | A | 4/1998 | Donadio, III et al. |
| 5,746,701 | A | 5/1998 | Noone |
| 5,769,830 | A | 6/1998 | Parker |
| 5,772,609 | A | 6/1998 | Nguyen et al. |
| 5,782,809 | A | 7/1998 | Umeno et al. |
| 5,788,653 | A | 8/1998 | Lorenzo |
| 5,788,654 | A | 8/1998 | Schwager |
| 5,788,707 | A | 8/1998 | Del Toro et al. |
| 5,792,124 | A | 8/1998 | Horrigan et al. |
| 5,797,856 | A | 8/1998 | Frisbie et al. |
| 5,800,454 | A | 9/1998 | Jacobsen et al. |
| 5,807,075 | A | 9/1998 | Jacobsen et al. |
| 5,807,249 | A | 9/1998 | Qin et al. |
| 5,810,885 | A | 9/1998 | Zinger |
| 5,813,996 | A | 9/1998 | St. Germain et al. |
| 5,827,225 | A | 10/1998 | Ma Schwab |
| 5,827,242 | A | 10/1998 | Follmer et al. |
| 5,833,632 | A | 11/1998 | Jacobsen et al. |
| 5,836,926 | A | 11/1998 | Peterson et al. |
| 5,843,050 | A | 12/1998 | Jones et al. |
| 5,843,244 | A | 12/1998 | Pelton et al. |
| 5,851,203 | A | 12/1998 | van Muiden |
| 5,895,378 | A | 4/1999 | Nita |
| 5,897,537 | A | 4/1999 | Berg et al. |
| 5,902,254 | A | 5/1999 | Magram |
| 5,902,290 | A | 5/1999 | Peacock, III et al. |
| 5,904,657 | A | 5/1999 | Unsworth et al. |
| 5,906,618 | A | 5/1999 | Larson, III |
| 5,911,715 | A | 6/1999 | Berg et al. |
| 5,911,717 | A | 6/1999 | Jacobsen et al. |
| 5,916,177 | A | 6/1999 | Schwager |
| 5,916,178 | A | 6/1999 | Noone |
| 5,916,194 | A | 6/1999 | Jacobsen et al. |
| 5,931,830 | A | 8/1999 | Jacobsen et al. |
| 5,935,108 | A | 8/1999 | Katoh et al. |
| 5,947,940 | A | 9/1999 | Beisel |
| 5,951,539 | A | 9/1999 | Nita et al. |
| 5,971,975 | A | 10/1999 | Mills et al. |
| 5,980,471 | A | 11/1999 | Jafari |
| 6,001,068 | A | 12/1999 | Uchino et al. |
| 6,004,279 | A | 12/1999 | Crowley et al. |
| 6,014,919 | A | 1/2000 | Jacobsen et al. |
| 6,017,319 | A | 1/2000 | Jacobsen et al. |
| 6,022,343 | A | 2/2000 | Johnson et al. |
| 6,022,369 | A | 2/2000 | Jacobsen et al. |
| 6,024,730 | A | 2/2000 | Pagan |
| 6,027,461 | A | 2/2000 | Walker et al. |
| 6,042,553 | A | 3/2000 | Solar et al. |
| 6,045,547 | A | 4/2000 | Ren et al. |
| 6,048,339 | A | 4/2000 | Zirps et al. |
| 6,056,702 | A | 5/2000 | Lorenzo |
| 6,063,101 | A | 5/2000 | Jacobsen et al. |
| 6,063,200 | A | 5/2000 | Jacobsen et al. |
| 6,066,361 | A | 5/2000 | Jacobsen et al. |
| 6,106,485 | A | 8/2000 | McMahon |
| 6,106,488 | A | 8/2000 | Fleming et al. |
| 6,139,510 | A | 10/2000 | Palermo |
| 6,165,292 | A | 12/2000 | Abrams et al. |
| 6,171,296 | B1 | 1/2001 | Chow |
| 6,183,410 | B1 | 2/2001 | Jacobsen et al. |
| 6,193,686 | B1 | 2/2001 | Estrada et al. |
| 6,197,014 | B1 | 3/2001 | Samson et al. |
| 6,203,485 | B1 | 3/2001 | Urick |
| RE37,148 | E | 4/2001 | Shank |
| 6,214,042 | B1 | 4/2001 | Jacobsen et al. |
| 6,228,073 | B1 | 5/2001 | Noone et al. |
| 6,248,082 | B1 | 6/2001 | Jafari |
| 6,251,092 | B1 | 6/2001 | Qin et al. |
| 6,254,549 | B1 | 7/2001 | Ramzipoor |
| 6,260,458 | B1 | 7/2001 | Jacobsen et al. |
| 6,273,404 | B1 | 8/2001 | Holman et al. |
| 6,273,876 | B1 | 8/2001 | Klima et al. |
| 6,273,879 | B1 | 8/2001 | Keith et al. |
| 6,290,656 | B1 | 9/2001 | Boyle et al. |
| 6,296,616 | B1 | 10/2001 | McMahon |
| 6,296,631 | B2 | 10/2001 | Chow |
| 6,302,870 | B1 | 10/2001 | Jacobsen et al. |
| 6,325,790 | B1 | 12/2001 | Trotta |
| 6,338,725 | B1 | 1/2002 | Hermann et al. |
| 6,346,091 | B1 | 2/2002 | Jacobsen et al. |
| 6,352,515 | B1 | 3/2002 | Anderson et al. |
| 6,355,005 | B1 | 3/2002 | Powell et al. |
| 6,355,027 | B1 | 3/2002 | Le et al. |
| 6,368,315 | B1 | 4/2002 | Gillis et al. |
| 6,368,316 | B1 | 4/2002 | Jansen et al. |
| 6,375,628 | B1 | 4/2002 | Zadno-Azizi et al. |
| 6,375,774 | B1 | 4/2002 | Lunn et al. |
| 6,379,369 | B1 | 4/2002 | Abrams et al. |
| 6,390,993 | B1 | 5/2002 | Cornish et al. |
| 6,398,758 | B1 | 6/2002 | Jacobsen et al. |
| 6,428,489 | B1 | 8/2002 | Jacobsen et al. |
| 6,428,512 | B1 | 8/2002 | Anderson et al. |
| 6,431,039 | B1 | 8/2002 | Jacobsen et al. |
| 6,440,088 | B1 | 8/2002 | Jacobsen |
| 6,478,778 | B1 | 11/2002 | Jacobsen et al. |
| 6,488,637 | B1 | 12/2002 | Eder et al. |
| 6,491,648 | B1 | 12/2002 | Cornish et al. |
| 6,491,671 | B1 | 12/2002 | Larson, III et al. |
| 6,503,244 | B2 | 1/2003 | Hayman |
| 6,508,803 | B1 | 1/2003 | Horikawa et al. |
| 6,524,301 | B1 | 2/2003 | Wilson et al. |
| 6,530,934 | B1 | 3/2003 | Jacobsen et al. |
| 6,547,779 | B2 | 4/2003 | Levine et al. |
| 6,553,880 | B2 | 4/2003 | Jacobsen et al. |
| 6,556,873 | B1 | 4/2003 | Smits |
| 6,579,246 | B2 | 6/2003 | Jacobsen et al. |
| 6,602,207 | B1 | 8/2003 | Mann et al. |
| 6,602,280 | B2 | 8/2003 | Chobotov |
| 6,610,046 | B1 | 8/2003 | Usami et al. |
| 6,623,448 | B2 | 9/2003 | Slater |
| 6,636,758 | B2 | 10/2003 | Sanchez et al. |
| 6,638,266 | B2 | 10/2003 | Wilson et al. |
| 6,652,508 | B2 | 11/2003 | Griffin et al. |
| 6,682,493 | B2 | 1/2004 | Mirigian |
| 6,689,120 | B1 | 2/2004 | Gerdts |
| 6,702,762 | B2 | 3/2004 | Jafari et al. |
| 6,712,826 | B2 | 3/2004 | Lui |
| 6,730,095 | B2 | 5/2004 | Olson, Jr. et al. |
| 6,749,560 | B1 | 6/2004 | Konstorum et al. |
| 6,766,720 | B1 | 7/2004 | Jacobsen et al. |
| 6,777,644 | B2 | 8/2004 | Peacock, III et al. |
| 6,811,544 | B2 | 11/2004 | Schaer |
| 6,837,898 | B2 | 1/2005 | Boyle et al. |
| 6,866,642 | B2 | 3/2005 | Kellerman et al. |
| 6,887,235 | B2 | 5/2005 | O'Connor et al. |
| 6,918,882 | B2 | 7/2005 | Skujins et al. |
| 6,997,937 | B2 | 2/2006 | Jacobsen et al. |
| 7,001,369 | B2 | 2/2006 | Griffin et al. |
| 7,074,197 | B2 | 7/2006 | Reynolds et al. |
| 7,153,277 | B2 | 12/2006 | Skujins et al. |
| 7,182,735 | B2 | 2/2007 | Shireman et al. |
| 7,785,274 | B2 * | 8/2010 | Mishima et al. ............... 600/585 |
| 2002/0013540 | A1 | 1/2002 | Jacobsen et al. |
| 2002/0019599 | A1 | 2/2002 | Rooney et al. |
| 2003/0009208 | A1 | 1/2003 | Snyder et al. |
| 2003/0060732 | A1 | 3/2003 | Jacobsen et al. |
| 2003/0069522 | A1 | 4/2003 | Jacobsen et al. |
| 2003/0216668 | A1 | 11/2003 | Howland et al. |
| 2004/0064069 | A1 | 4/2004 | Reynolds et al. |
| 2004/0116831 | A1 | 6/2004 | Vrba |
| 2004/0142643 | A1 | 7/2004 | Miller et al. |

| | | | | | | |
|---|---|---|---|---|---|---|
| 2004/0167436 | A1 | 8/2004 | Reynolds et al. | JP | 5-309159 | 11/1993 |
| 2004/0167437 | A1 | 8/2004 | Sharrow et al. | JP | 5-507857 | 11/1993 |
| 2004/0167441 | A1 | 8/2004 | Reynolds et al. | JP | 6-501179 | 2/1994 |
| 2004/0181174 | A2 | 9/2004 | Davis et al. | JP | 631749 | 4/1994 |
| 2004/0181176 | A1 | 9/2004 | Jafari et al. | JP | 6169996 | 6/1994 |
| 2006/0121218 | A1 | 6/2006 | Obara et al. | JP | 6-63224 | 9/1994 |
| 2006/0122537 | A1 | 6/2006 | Reynolds et al. | JP | 6312313 | 11/1994 |
| 2006/0189896 | A1 | 8/2006 | Davis et al. | JP | 728562 | 5/1995 |
| 2006/0264904 | A1 | 11/2006 | Kerby et al. | JP | 7124164 | 5/1995 |
| 2008/0021347 | A1 | 1/2008 | Jacobsen et al. | JP | 7124263 | 5/1995 |
| 2008/0021348 | A1 | 1/2008 | Jacobsen et al. | JP | 7136280 | 5/1995 |
| 2008/0021400 | A1 | 1/2008 | Jacobsen et al. | JP | 7148264 | 6/1995 |
| 2008/0021401 | A1 | 1/2008 | Jacobsen et al. | JP | 7505561 | 6/1995 |
| 2008/0021402 | A1 | 1/2008 | Jacobsen et al. | JP | 7037199 | 7/1995 |
| 2008/0021403 | A1 | 1/2008 | Jacobsen et al. | JP | 7185009 | 7/1995 |
| 2008/0021404 | A1 | 1/2008 | Jacobsen et al. | JP | 7255855 | 10/1995 |
| 2008/0021405 | A1 | 1/2008 | Jacobsen et al. | JP | 7275366 | 10/1995 |
| 2008/0021406 | A1 | 1/2008 | Jacobsen et al. | JP | 751067 | 11/1995 |
| 2008/0021407 | A1 | 1/2008 | Jacobsen et al. | JP | 8-229888 | 9/1996 |
| 2008/0021408 | A1 | 1/2008 | Jacobsen et al. | JP | 8509141 | 10/1996 |
| 2008/0077119 | A1 | 3/2008 | Snyder et al. | JP | 8317988 | 12/1996 |
| 2008/0183182 | A1* | 7/2008 | Satou et al. ............ 606/108 | JP | 9000164 | 4/1997 |
| | | | | JP | 9-276413 | 10/1997 |

FOREIGN PATENT DOCUMENTS

| | | | | | |
|---|---|---|---|---|---|
| | | | JP | 9276413 | 10/1997 |
| AU | | 733966 | 4/1998 | JP | 9-294813 A | 11/1997 |
| BR | PI | 9712829 | 1/2000 | JP | 9294813 | 11/1997 |
| CA | | 2266685 | 5/2006 | JP | 10-118193 | 5/1998 |
| CA | | 2255781 | 3/2007 | JP | 10328191 | 12/1998 |
| CN | | 1230914 | 10/1999 | JP | 11-267224 A | 10/1999 |
| DE | | 2539191 | 3/1976 | JP | 2000-197704 A | 7/2000 |
| DE | | 285514 | 12/1990 | JP | 2000-510722 A | 8/2000 |
| EP | | 0 045 931 | 2/1982 | JP | 2000-511083 A | 8/2000 |
| EP | | 0 069 522 | 1/1983 | JP | 2001-500808 A | 1/2001 |
| EP | | 0 087 933 | 9/1983 | JP | 3325828 | 7/2002 |
| EP | | 0 111 044 | 6/1984 | JP | 2002-529137 A | 9/2002 |
| EP | | 0 181 174 | 5/1986 | JP | 2002-542901 A | 12/2002 |
| EP | | 0 377 453 | 7/1990 | JP | 2002-543896 A | 12/2002 |
| EP | | 0 565 065 | 6/1996 | JP | 2003-517893 A | 6/2003 |
| EP | | 0 778 038 | 6/1997 | JP | 3649604 | 2/2005 |
| EP | | 0 778 039 | 6/1997 | JP | 2005-534407 | 11/2005 |
| EP | | 0 778 040 | 6/1997 | SU | 712908 | 1/1980 |
| EP | | 0 812 599 | 12/1997 | SU | 758421 | 8/1980 |
| EP | | 0 865 772 | 9/1998 | SU | 1529365 | 12/1989 |
| EP | | 0 865 773 | 9/1998 | WO | WO 90/02520 | 3/1990 |
| EP | | 0 521 595 | 5/1999 | WO | WO 91/13364 | 9/1991 |
| EP | | 0 917 885 | 5/1999 | WO | WO 92/04072 | 3/1992 |
| EP | | 0 937 481 | 8/1999 | WO | WO 92/07619 | 5/1992 |
| EP | | 0982046 | 3/2000 | WO | WO 93/04722 | 3/1993 |
| EP | | 0 790 066 | 4/2000 | WO | WO 93/11313 | 6/1993 |
| EP | | 0 608 853 | 4/2003 | WO | WO 95/24236 | 9/1995 |
| EP | | 0 935 947 | 12/2004 | WO | WO 96/19255 | 6/1996 |
| EP | | 1498152 | 1/2005 | WO | WO 97/10022 | 3/1997 |
| EP | | 0 934 141 | 11/2005 | WO | WO 97/25914 | 7/1997 |
| EP | | 1685869 | 8/2006 | WO | WO 97/43949 | 11/1997 |
| GB | | 2214354 | 8/1989 | WO | WO 97/44083 | 11/1997 |
| GB | | 2257269 | 1/1993 | WO | WO 97/44086 | 11/1997 |
| JP | | 58-8522 | 1/1983 | WO | WO 98/10694 | 3/1998 |
| JP | | 60091858 | 5/1985 | WO | WO 99/04847 | 2/1999 |
| JP | | 61022752 | 1/1986 | WO | WO 99/11313 | 3/1999 |
| JP | | 62023361 | 1/1987 | WO | WO 00/27303 | 5/2000 |
| JP | | 62089470 | 4/1987 | WO | WO 00/30710 | 6/2000 |
| JP | | 62299277 | 12/1987 | WO | WO 00/48645 | 8/2000 |
| JP | | 6393516 | 4/1988 | WO | WO 00/57943 | 10/2000 |
| JP | | 63-181774 | 7/1988 | WO | WO 00/66199 | 11/2000 |
| JP | | 63217966 | 9/1988 | WO | WO 00/67845 | 11/2000 |
| JP | | 1089956 | 4/1989 | WO | WO 00/72907 | 12/2000 |
| JP | | 1135363 | 5/1989 | WO | WO 01/28620 | 4/2001 |
| JP | | 1158936 | 6/1989 | WO | WO 01/36034 | 5/2001 |
| JP | | 2107268 | 4/1990 | WO | 0145912 | 6/2001 |
| JP | | 3081831 | 4/1991 | WO | WO 01/45773 | 6/2001 |
| JP | | 03-122850 | 12/1991 | WO | WO 01/93920 | 12/2001 |
| JP | | 4061840 | 2/1992 | WO | WO 02/013682 | 2/2002 |
| JP | | 4099963 | 3/1992 | WO | WO 02/062540 | 8/2002 |
| JP | | 4213069 | 8/1992 | WO | WO 03/004086 | 1/2003 |
| JP | | 4213070 | 8/1992 | WO | WO 03/008148 | 1/2003 |
| JP | | 4236965 | 8/1992 | WO | WO 2004/012804 | 2/2004 |
| JP | | 5149969 | 6/1993 | WO | 2004047899 | 6/2004 |
| JP | | 5-506806 | 10/1993 | | | |

* cited by examiner

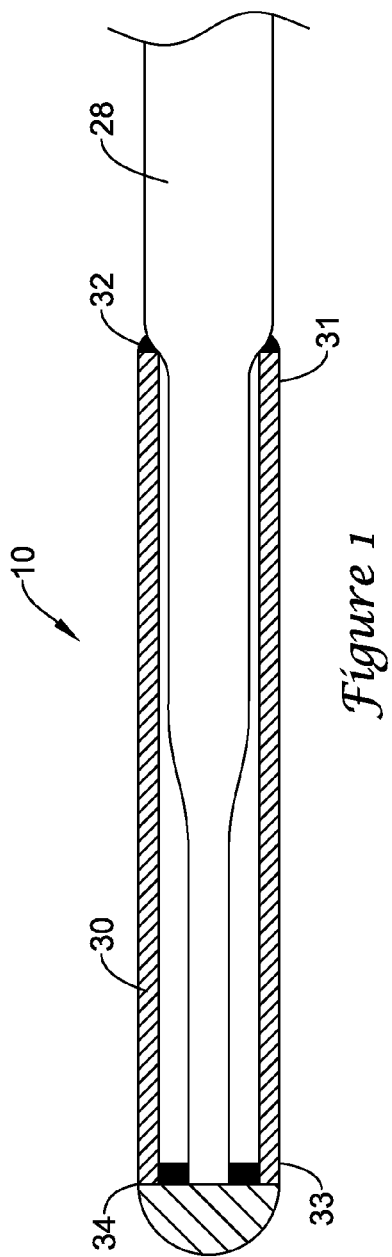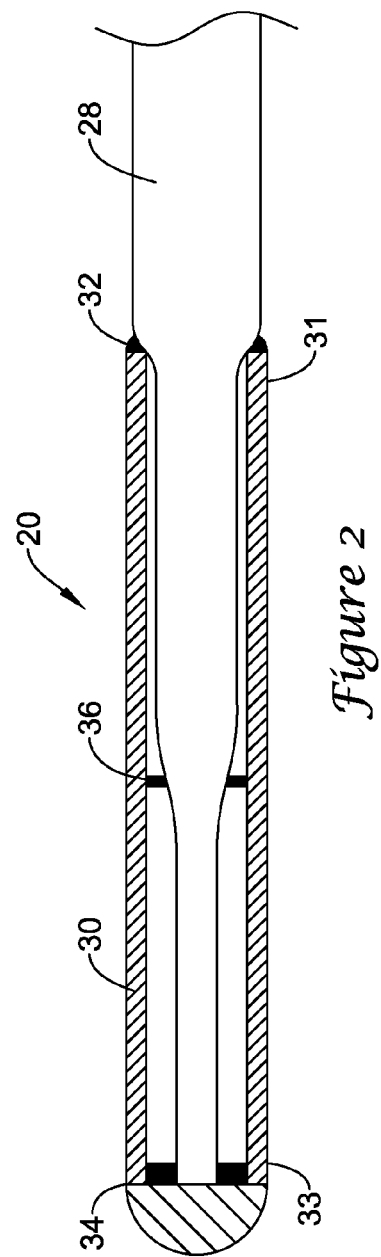

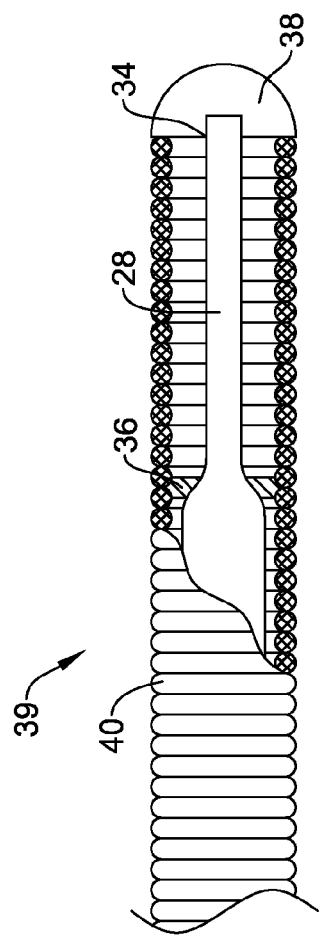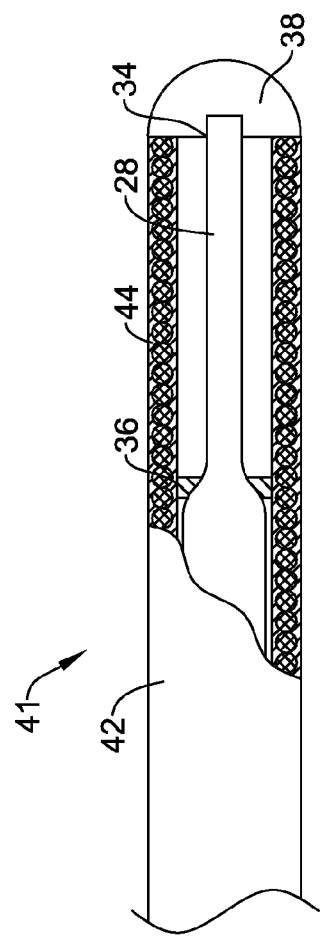
Figure 8
Figure 9

ELONGATE MEDICAL DEVICE HAVING ENHANCED TORQUE AND METHODS THEREOF

FIELD

This invention relates generally to medical devices for navigating through anatomy such as intravascular systems and methods of manufacture thereof.

BACKGROUND

Medical devices such as endovascular or intravascular devices have been used for many years for purposes such as performing various medical procedures. For example, a medical device such as a guidewire or catheter may be used to navigate through the tortuous anatomy of a patient to reach an area of interest and guide other medical devices thereto to perform one or more therapeutic procedures. A medical device may be introduced into a patient's anatomy or vasculature at a relatively accessible location such as a femoral, brachial or other suitable artery, and guided through the patient's anatomy to the desired location. Often fluoroscopy or other imaging techniques are used to observe a portion of the medical device such as the tip to aid in navigation. The medical device may be rotated at bifurcations in the anatomy before being advanced to guide the medical device to the desired location.

It is often desirable that a medical device such as an intravascular device to be laterally flexible such that it can bend easily in order to allow it to navigate the often tortuous anatomy of a patient and to minimize trauma to the patient. It is often also desirable that such medical devices have relatively stiff torsional characteristics to permit control of the device when navigating it through the anatomy. A number of different medical devices having flexibility and torsional stiffness characteristics are known, each having certain advantages and disadvantages. However, there is an ongoing need to provide alternative elongated medical device structures and assemblies.

SUMMARY OF SOME EXAMPLE EMBODIMENTS

The invention provides design, material, and manufacturing method alternatives for medical devices. One embodiment pertains to an intravascular medical device having a longitudinal axis comprising a first elongate member having a first end, a second end, and a lumen disposed there between. A second elongate member can be disposed in the lumen of the first elongate member and fastened to the first elongate member at the first end, the second end, and at a location between the two ends selected using the Method for Enhancing the Ratio of Torsional Stiffness to Transverse Flexibility described below. In some embodiments, the first elongate member may be a tubular member such as a slotted or grooved hypotube where the slots or grooves are configured to make the first elongate member more flexible about an axis normal to the longitudinal axis. In some other embodiments, the first elongate member may be a coil such as a coil made from a wire or a flat ribbon, and may have uniform spacing, distally increasing spacing or sections with different spacing. In some embodiments, the coil may be disposed or imbedded in a tube such as a polymer tube. The second elongate member may be a core such as a core wire and may have a uniform or non-uniform cross-section along its length such as a distally tapering cross-section. It may have a circular cross-section or a non-circular cross-section such as a polygonal cross-section and may include one or more cross-sectional shapes along its length. The medical device may be a guidewire, catheter, or a distal protection device including a filter, or other medical device. The connection may be made using an adhesive, a weld, a laser weld, a solder, a braze, mechanical fit or other suitable means.

Some example embodiments pertain to an elongate medical device such as a guidewire comprising a first elongate member having a proximal end a distal end and a lumen there between. A second elongate member having a proximal end and a distal end is at least partially disposed in the first elongate member. A first connection between the first elongate member and the second elongate member may be disposed adjacent the proximal end of the first elongate member, a second connection between the first elongate member and the second elongate member may be disposed adjacent the distal end of the first elongate member, and a third connection between the first elongate member and the second elongate member may be disposed between the first and second connections. The third connection may be at a position to optimize the torsional rigidity of the device or within 10%, 5% or 2% of the distance between the first and second attachments of a point where the connection would provide maximum torsional stiffness. Such a point may be determined by empirical experimentation, software analysis or torsional spring modeling. The second elongate member may be a core such as a core wire and may comprise a super-elastic material such as a nickel-titanium alloy and may have varied or distal decreasing cross-sectional areas. The first elongate member may be a tube or sleeve, for example, and may be a tube or sleeve with a plurality of slots disposed therein (a tube with a plurality of slots disposed at an orientation normal to the longitudinal axis of the tube, for example). The third connection point may be a solid connection such as that formed by adhesive, solder, welding or the like or it may be a connection designed merely to limit the relative rotation of the first and second elongate members about the longitudinal axis. The third connection may include a collar fixed to the second elongate member at the third connection point and an insert fixed to the first elongate member at the third connection point where the insert defines an open space in which the collar is disposed and through which the collar may move longitudinally but in which the collar is restrained from rotating about the longitudinal axis relative to the insert. Such a collar may have an elliptical, cruciform or other suitable cross-sectional periphery and the insert may have a correspondingly shaped lumen.

The above summary of some embodiments is not intended to describe each disclosed embodiment or every implementation of the present invention. The Figures, and Detailed Description which follow more particularly exemplify some of these embodiments.

BRIEF DESCRIPTION OF DRAWINGS

The invention may be more completely understood in consideration of the following detailed description of various embodiments of the invention in connection with the accompanying drawings, in which:

FIG. 1 is a cross-sectional diagrammatic view of an elongate medical device;

FIG. 2 is a cross-sectional diagrammatic view of a second elongate medical device;

FIG. 5b is a partial longitudinal cross-sectional view of the elongate medical device of FIG. 5a;

FIG. 8 is partial cross-sectional view of the distal portion of an elongate medical device;

FIG. 9 is partial cross-sectional view of the distal portion of an elongate medical device.

Figure 3:
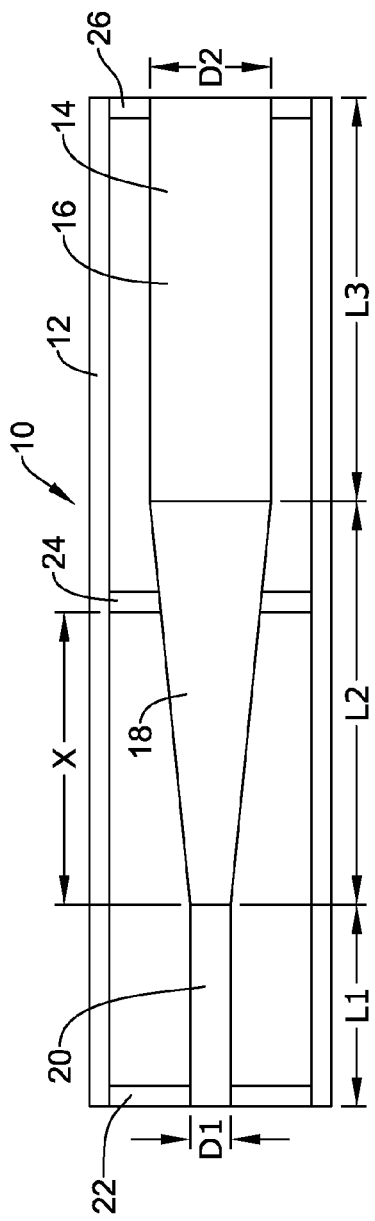
FIG. 3 is a cross-sectional diagrammatic view of an elongate medical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100

The recitation of numerical ranges by endpoints includes all numbers within that range (e.g. 1 to 5 includes 1, 1.5, 2, 2.75, 3, 3.80, 4, and 5)

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise The following detailed description should be read with reference to the drawings in which similar elements in different drawings are numbered the same. The drawings, which are not necessarily to scale, depict illustrative embodiments and are not intended to limit the scope of the invention.

FIG. 1 is a partial cross-sectional diagrammatic view of the distal portion of an elongate medical device such as a guidewire 10. The medical device includes a first elongate member, such as core 28, and a second elongate member, such as a tube and/or sleeve 30. The sleeve 30 is attached to the core 28 at first connection 32 and second connection 34, which may be adhesive, welds, solder, brazing, mechanical interlocking or crimping, or other suitable attachments. The core 28 may have a distally decreasing diameter, for example, to increase flexibility. However, as one increases flexibility in this manner, there may be a corresponding decrease in torsional stiffness. Such a decrease in torsional stiffness may make it more difficult to maneuver through the tortuous lumens of a patient's vasculature. For example, if a guidewire is less torsionally stiff, when a user twists the proximal end of the guidewire, there may be a significant lag or delay in transmission as well as a reduction in the amount of twist imparted to the distal end. In other words, if a guidewire is less torsionally stiff, when a user inputs angular displacement to the proximal end of the guidewire, there may be a significant decrease in transmitting the displacement/angular input to the distal end. In some cases, much of the twist (e.g. displacement or angular input) from the proximal end may not be transmitted to the distal end at all. Such a guidewire is more likely to be twisted, jammed or kinked when manipulated. One method of increasing the torsional stiffness without a proportional decrease in flexibility is to dispose and connect a tube or sleeve structure such as sleeve 30 about the core 28, for example, as shown in the embodiment of FIG. 1.

An example method of further enhancing the torsional stiffness of an elongate medical device is illustrated in FIG. 2, which is a partial cross-sectional diagrammatic view of the distal portion of an example elongate medical device such as a guidewire 20. The medical device of FIG. 2 includes core 28, sleeve 30, first connection 32 between core 28 and sleeve 30 and second connection 34 between core 28 and sleeve 30. In this embodiment, connections 32 and 34 are disposed proximate the proximal and distal ends 31/33, respectively, of sleeve 30, and may provide for enhanced torsional stiffness of the guidewire 20. In another example embodiment, the connections 32 and 34 are at the proximal and distal ends 31/33 of the sleeve 30, respectively. Other embodiments may have different design criteria and locate these connections elsewhere. A third connection 36 attaches core 28 and sleeve 30 at a location between first connection 32 and second connection 34. Third connection 36 may be at any location along the length of the sleeve 30 between the first and second connections 32/34, but in at least some embodiments, the location of the third connection 36 can be positioned to better obtain desirable torque characteristics, as will be discussed in more detail below.

In this embodiment, connections 32, 34 and 36 limit relative movement between the sleeve 30 and the core 28 at the connections points along all six degrees of freedom. In other words, they can be solid. Such connections may be made using any suitable technique, such as welding, soldering, brazing, adhesive bonding, mechanical attachment or fitting or the like. As described below, other connection types are contemplated. At both connection 32 and connection 34, the core 28 is depicted as centered within the sleeve 30. This coaxial configuration is but one of the contemplated configurations. For example, in other contemplated embodiments the core 28 could essentially lay along one side of the sleeve along the length of the sleeve 30, or the core could be centered in the sleeve 30 at the proximal end 31 of the sleeve 30 and positioned eccentrically within the sleeve 30 at the distal end 33 of the sleeve 30.

In the embodiment of FIG. 2, core 28 is a solid core having three successively narrower sections of uniform diameter. The two transition sections smoothly taper from one section to the next. Each transition section, therefore, has a continuously changing transverse cross-section. As will be appreciated, however, in some embodiments, the core 28 may not include such tapered sections, while in other embodiments, may have a different taper configuration, as desired. The core 28 may be made of or include any suitable material, for example, a superelastic nickel-titanium alloy or other suitable material or materials as described below, or others.

Sleeve 30 may be a tube or other suitable member and its materials and geometry may be selected to improve torque transmission as describe below. Such a sleeve 30 may be, for example, a solid or slotted hypotube, such as a metallic hypotube, a coil, and/or may be made from a polymer or other suitable material as described below.

Figure 5A:
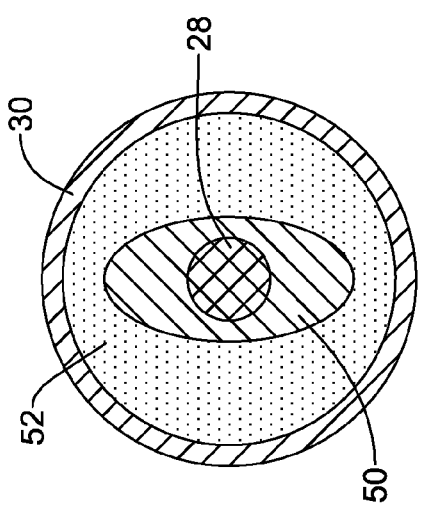
FIG. 5a is a transverse cross-sectional view of an example elongate medical device.
Figure 5B:
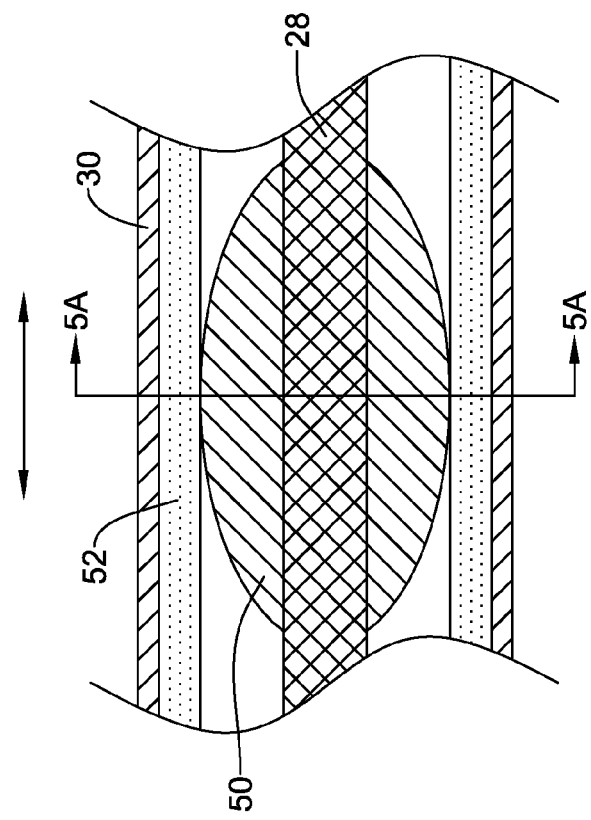

By connecting the core 28 and the sleeve 30 at a third connection 36 between the first two connections 32/34, the torsional stiffness of the medical device is enhanced. Third connection 36 at least prevents relative rotational movement of the core 28 and the sleeve 30 about the longitudinal axis of the device. As such, it may be a solid connection between the sleeve 30 and the core 28. In some embodiments, the connection 36 may also permit relative longitudinal movement of the core 28 and the sleeve 30 while still limiting the relative rotational movement of the core 28 and the sleeve 30. Such a connection may involve an elliptical collar fixed to and surrounding the core 28 and a corresponding insert affixed to the sleeve 30 and having an elliptical hole to receive the collar. The collar and the insert could still slide with respect to each other. The insert may have a uniform profile lengthwise or it may have an oviform profile. An example of such a connection is illustrated in FIGS. 5A and 5B which are a transverse cross section and a partial longitudinal cross section of such a connection. The double-headed arrow of FIG. 5B illustrates the direction of relative movement between core 28 and sleeve 30 allowed by the connection. Elliptical collar 50 can be affixed to core 28 and corresponding insert 52 can be affixed to tube 30. Of course, many variations are possible. The collar 50 could have a cruciform or stelliform cross-section, for example, and the insert 52 may have a corresponding hole for the collar to fit into.

In at least some embodiments, it is contemplated that third connection 36 extends longitudinally only so far as to provide a secure bond between the core 28 and the sleeve 30. In other words, third connection may be along the lines of a point connection. In other embodiments, third connection 36 may extend longitudinally beyond what is necessary to provide a bond. It may extend longitudinally, for example, to alter the bending characteristics of the medical device.

Third connection 36 may be positioned at any point between the first two connections 32/34 as desired. However, for a given core 28 and tube 30 that are connected together at two initial spaced connections or at the ends 31/33 of the tube 30, there is an attachment point for the third connection 36 that will maximize the torsional stiffness. This optimal attachment point location may be selected using the Method for Enhancing the Ratio of Torsional Stiffness to Transverse Flexibility as described below or may be selected using another suitable technique such as finite element analyses or other techniques such as empirical experimentation The third connection 36 of the embodiment of FIG. 2 may be at this optimal attachment point location or may be at a location within 10%, 5%, 2%, 1% or 0.5% of the distance between the first and second attachment points 32/34 of this optimal attachment point location. The location of such an attachment point can be dependent upon the particulars of the medical device. Changes in materials and dimensions may change the location of the attachment point that maximizes torsional stiffness. This third connection point 36 may be advantageous in not only providing additional torque to the tip of the medical device but in providing additional torque against resistance at other locations along the medical device.

In some embodiments, a gap or space remains open or unfilled by any other structure of the guide wire along substantially the entire length of the tube 30, with the exception of the connection points, e.g. 32/34/36. For example, in some embodiments, the gap or space can extend between the outer surface of the core 28 and the inner surface of the tube 30 along the length of the tube 30 in the range of about 50% or greater, 75% or greater, 90% or greater, or 95% or greater of the entire length of the tube 30. However, even in other embodiments with additional attachment points along the length of the tube 30, the overall gap or space may still collectively extend along a substantial portion of the length of the tube 30, for example, in percentages of the total length as given above. As such, the tube 30 can act to reinforce or impart desired properties, such as torsional rigidity, to the core 28, but allow at least the portion of the core 28 surrounded by the gap or space to move laterally within the lumen and retain transverse flexibility. Transverse flexibility is flexibility about an axis normal to the longitudinal axis.

The Method for Enhancing the Ratio of Torsional Stiffness to Transverse Flexibility is an algorithm that may be applied to design elongate medical devices of varying configurations. Generally the method can involve the following steps. One divides the components into sections for which equations for the spring constants may be written. For example, different portions of the different components will have different spring constants. As such different equations can be written for portions having different spring constants. For example, one equation may be written for a straight section of core 28 and a second equation may be written for a tapered section of core 28. One then makes an initial assumption about which section the optimal third connection location may lie on. The equations may then be written in relation to this optimal third connection location as described in more detail below. These spring constant equations for the medical device may be related to each other by modeling the medical device as a plurality of torsional springs in series and in parallel. One can use the series and parallel spring equations to get a spring constant equivalent to the device. This equation is then differentiated with respect to the third connection location to determine a potential optimal third connection location. One may then check the initial section assumption. For example, the location determined by this equation may be at a local minimum rather than at a local maximum or the location may be at an extremity of the section, which may indicate that the section assumption was erroneous. One or more different section assumptions may be made and the process may be repeated to corroborate or correct previous results. This iterative process will verify a correct optimal third connection location or eliminate an erroneous location and reveal a new potential third connection location. The third connection may then be made at this location or within a predetermined distance from this location. For example, if the distance between the first connection and the second connection is a given length, the third connection may be made within 10%, 5%, 2%, 1% or 0.5% of that given length to the determined optimum connection location. Because the third connection location can be or is near optimal for enhancing torsional stiffness, most of the space between the tube 30 and the core 28 may remain unfilled to maintain transverse flexibility.

An example Method for Enhancing the Ratio of Torsional Stiffness to Transverse Flexibility is illustrated for the medical device of FIG. 2. This medical device 10 can be depicted schematically as in FIG. 3, with sleeve 12 and core 14. Core 14 has a proximal section 16 having diameter D2 and length L3, a distally tapering middle section 18 having proximal diameter D2, distal diameter D1 and length L2 and distal section 20 having diameter D1 and length L1. Beginning with the assumption that the optimal third connection location is at the middle section 18, sleeve 12 and core 14 are connected at connections 22, 24 and 26. Connections 22 and 26 are at or adjacent to the distal and proximal ends of sleeve 12, respectively. Connection 24 is the distance X+L1 proximally from the distal end of the medical device. One assumption underlying this model is that the third connection 24 will fall somewhere on the middle section 18. Other models assuming the connection will fall on the proximal or distal sections may be constructed to verify the optimal placement of this third connection.

Figure 4:
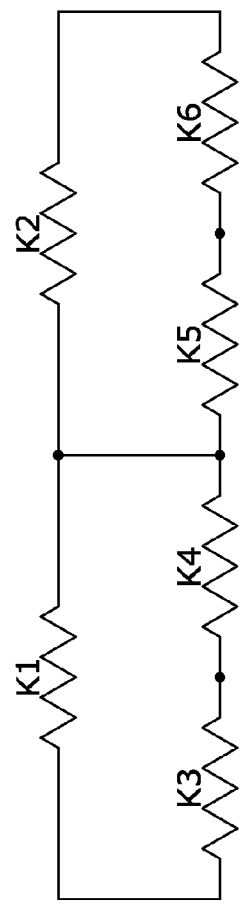
FIG. 4 is a diagrammatic view of an elongate medical device modeled as a plurality of springs.

This medical device can then be modeled as FIG. 4, where the various sections are modeled as torsional spring constants in series and parallel. K1 and K2 are the spring constants of sleeve 12 distal and proximal of connection 24, respectively. K3 and K6 are the spring constants of the distal section 20 and the proximal section 16. K4 and K5 are the spring constants of the portions of the middle section 18 distal and proximal of connection 24, respectively. Knowing the equation for the equivalent spring constant for springs in series to be $$\frac{1}{K_1} + \frac{1}{K_2} = \frac{1}{K_{eq}}$$

and the equation for the equivalent spring constant of springs in parallel to be $K_1+K_2=K_{eq}$, one can create the equations for the spring constant equivalent to the spring constants in FIG. 4.

$$K34_{eq} = \frac{K3 \cdot K4}{K3 + K4}$$

and $$K56_{eq} = \frac{K5 \cdot K6}{K5 + K6},$$

$$K134_{eq} = K1 + \frac{K3 \cdot K4}{K3 + K4}$$

and $$K256_{eq} = K2 + \frac{K5 \cdot K6}{K5 + K6}.$$

The equation for the overall equivalence is then $$K_{eq} = \frac{K134_{eq} \cdot K256_{eq}}{K134_{eq} + K256_{eq}}$$

which is the quantity we want to maximize. To relate the location of the third connection point to the spring constants, one can determine individual spring constants as a function of the position of bond 24 empirically, through finite element analysis or through mechanics of materials equations.

$$K = \frac{G \cdot J}{L}$$

where G is the shear modulus, J is the polar moment of inertia, the product GJ is the torsional rigidity, and L is the length of the section. G is a function of the material and J is a function of the cross-sectional geometry. We can begin writing equations relating various K values and the position of connection 24. It simplifies the math to derive equations for $\Theta$, which is the inverse of the spring constant K. Thus, for section 16 of the core, the equation $$\frac{1}{K6} = \Theta_6 = \frac{L3}{G \cdot J} = \frac{32 \cdot L3}{G \cdot \pi \cdot D2^4}$$

relates the geometry and the materials to the K values. For section 18 proximal to connection 24, the equation $$\frac{1}{K5} = \Theta_5$$

$$= \int_x^{L2} \frac{1}{G \cdot J(x)} dx$$

$$= \int_x^{L2} \frac{32}{G \cdot \pi \cdot D(x)^4} dx$$

$$= \int_x^{L2} \frac{32}{G \cdot \pi \cdot \left(D1 + \left(\frac{D2-D1}{L2}\right)x\right)^4} dx$$

relates the geometry and the materials to the K values. Other equations can be derived similarly. One can then plug these and other equations for the individual spring constants into the equation for the equivalent spring constant. One then differentiates the resultant equation, sets it equal to 0 and solves for x, which is the position of connection 24. A check must be made to ensure that x results in a maximum torsional stiffness value rather than a minimum. This can be done by verifying that the second derivative of the function is negative, not positive, where the function's first derivative equals 0. Further the result may indicate that an incorrect assumption was made regarding which section of the core or the sleeve the optimal position of connection 24 would fall upon. If this is the case, that assumption must be revised and the above process repeated. Through this Method for Enhancing the Ratio of Torsional Stiffness to Transverse Flexibility, one can arrive at an optimal position of connection 24 to maximize the torsional stiffness of the medical device. As such, the connection 24 can be then made at this point or within a predetermined distance from this point. For example, the connection may be made within 15%, 10%, 5%, 2%, 1%, 0.5% or less of the distance between the connection points 22 and 26 from the optimal location.

In some embodiments, more than three connection points are contemplated. One example medical device includes a core, a sleeve, a connection between the core and the sleeve at the proximal end of the sleeve, a connection between the core and the sleeve at the distal end of the sleeve, and two connections spaced apart from each other and from the first two connections and between the first two connections. The spacing of these two connections may be as desired or may be selected to optimize the torsional stiffness of the device. A process such as that described above may be used to select the optimal positions of the medial two connections. Because there are two variables to solve for, an iterative process may be set up solving for one of the variables at various values of the other variable. For example, the position of a third connection point between the first connection point and the second connection point is assumed. The position of a fourth connection point is solved for using the Method for Enhancing the Ratio of Torsional Stiffness to Transverse Flexibility as described above. A different position for the third connection point is assumed and the position of a fourth connection point is solved for. In one example, at each millimeter between the first and second connection points, a third connection point is assumed and a fourth connection point is solved for. The locations that result in a maximum torsional stiffness are then selected and the connections can be made, for example, within 15%, 10%, 5%, 2%, 1%, 0.5% or less of the distance between the connection points 22 and 26 from the optimal locations. Such an iterative process can be easily set up using any number of standard computer software packages.

Figure 6:
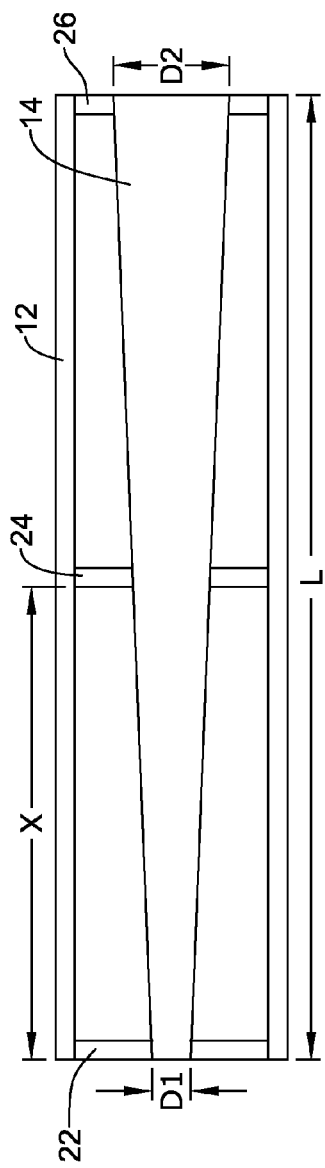
FIG. 6 is a cross-sectional diagrammatic view of an elongate medical device.
Figure 7:
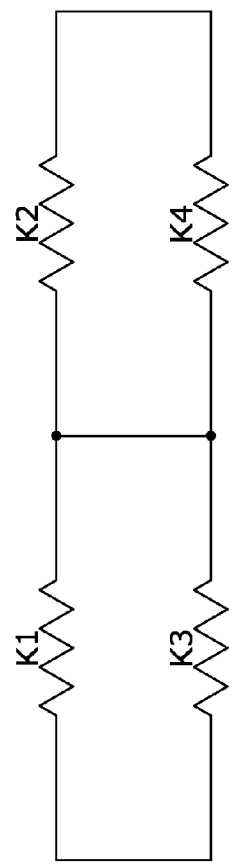
FIG. 7 is a diagrammatic view of an elongate medical device modeled as a plurality of springs.

Another illustration of the Method for Enhancing the Ratio of Torsional Stiffness to Transverse Flexibility is given for the guidewire illustrated diagrammatically in FIG. 6 which has a single core 14 of uniform taper disposed in tube 12. The tube 12 and core 14 are connected distally and proximally at locations 22 and 26 and medially at point 24. The location of point 24 is, of course, determined by the Method for Enhancing the Ratio of Torsional Stiffness to Transverse Flexibility. The guidewire may be modeled as a plurality of torsional springs connected in parallel and series as shown in FIG. 7. One can determine values for K1 and K2 as described above. The equation for the spring constant of the section of wire 14 proximal to connection 24 is $$\frac{1}{K4} = \Theta_4$$
$$= \int_x^L \frac{1}{G \cdot J(x)} dx$$
$$= \int_x^L \frac{32}{G \cdot \pi \cdot D(x)^4} dx$$
$$= \int_x^L \frac{32}{G \cdot \pi \cdot \left(D1 + \left(\frac{D2 - D1}{L}\right)x\right)^4} dx.$$

The equation for the section of wire 14 distal to connection 24 is $$\frac{1}{K3} = \Theta_3$$
$$= \int_0^x \frac{1}{G \cdot J(x)} dx$$
$$= \int_0^x \frac{32}{G \cdot \pi \cdot D(x)^4} dx$$
$$= \int_0^x \frac{32}{G \cdot \pi \cdot \left(D1 + \left(\frac{D2 - D1}{L2}\right)x\right)^4} dx.$$

These equations can be related using the equation for the spring equivalent constant, which using the series and parallel laws described above is:

$$K_{eq} = \frac{(K1 + K3)(K2 + K4)}{K1 + K3 + K2 + K4}.$$

One differentiates the equation with respect to x to find the potential optimal location for connection 24.

Of course, embodiments of medical devices are contemplated that have other elements. For example a lubricious sleeve including a material such as a polymer, elastomer, polyurethane, polyethylene, Teflon or other suitable material may be disposed over the medical device or over the sleeve. In some embodiments, the sleeve may be embedded or partially embedded therein. Some embodiments may include radiopaque materials disposed in certain components or at selected spots to enhance visibility of the device with x-ray fluoroscopy. For example a marker band may be disposed on the wire at the distal end of the device. Such a marker band may include a radiopaque material such as platinum, gold, tungsten, iridium, rhodium and alloys thereof such as platinum tungsten alloys or platinum iridium rhodium alloys. Some embodiments may include an MRI detectable element such as gadolinium, a gadolinium compound, gadolinium encapsulated in a sheath, dysprosium or dysprosium encapsulated in a sheath. Other components may include a distal protection device such as a filter, a tensile fiber extending from the distal tip through the sleeve and attached at a proximal point, or an atraumatic distal tip or distal tip coil.

FIG. 8 is a partial cross-sectional view of the distal portion of a guidewire 39 according to an embodiment of the invention. The guidewire includes a core 28 disposed in the central lumen of a sleeve 40. Sleeve 40 is depicted as a coil though other sleeves are possible as described above. Core 28 and sleeve 40 are connected at a proximal connection point at the proximal end of the sleeve (not pictured), at a distal connection point 34 at atraumatic distal tip 38 and at a medial connection point 36. It is contemplated that connection point 36 is at a location that optimizes the torsional stiffness of the guidewire, the location determined by using a Method for Enhancing the Ratio of Torsional Stiffness to Transverse Flexibility as discussed above, or within 15%, 10%, 5%, 2%, 1%, 0.5% or less of the distance between the connection points 22 and 26 from the optimal location.

FIG. 9 is a partial cross-sectional view of the distal portion of a guidewire 41 according to another embodiment. The guidewire includes a core 28 disposed in the central lumen of a sleeve 42. Sleeve 42 is depicted as a polymer tube with coils 44 having a variable spacing to vary the bending characteristics embedded therein. Core 28 and sleeve 42 are connected at a proximal connection point at the proximal end of the sleeve (not pictured), at a distal connection point 34 at atraumatic distal tip 38 and at a medial connection point 36. It is contemplated that connection point 36 is at a location that optimizes the torsional stiffness of the guidewire, the location determined using a Method for Enhancing the Ratio of Torsional Stiffness to Transverse Flexibility as discussed above, or within 15%, 10%, 5%, 2%, 1%, 0.5% or less of the distance between the connection points 22 and 26 from the optimal location.

Figure 10:
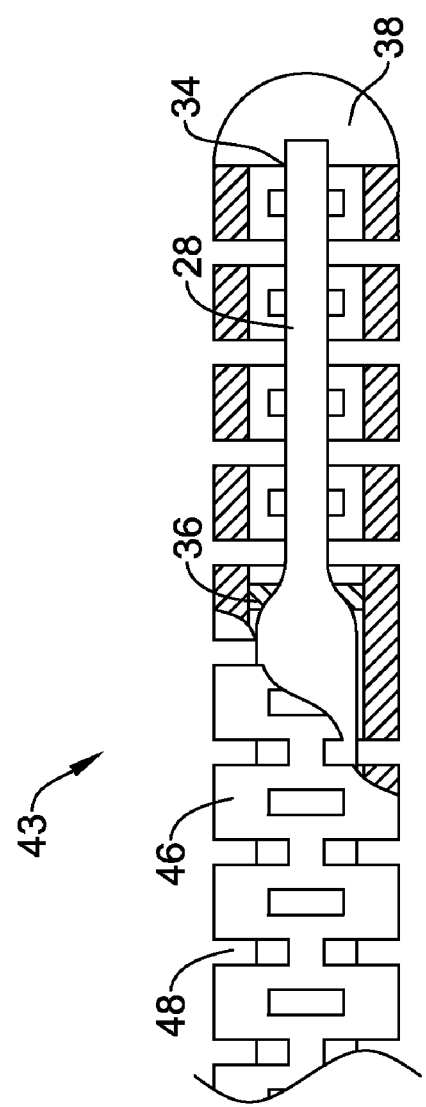
FIG. 10 is partial cross-sectional view of the distal portion of an elongate medical device.

FIG. 10 is a partial cross-sectional view of the distal portion of a guidewire 43 according to an embodiment of the invention. The guidewire includes a core 28 disposed in the central lumen of a sleeve 46. Sleeve 46 is depicted as a metallic or polymer tube with slots 48 cut there from. Core 28 and sleeve 46 are connected at a proximal connection point at the proximal end of the sleeve (not pictured), at a distal connection point 34 at atraumatic distal tip 38 and at a medial connection point 36. It is contemplated that connection point 36 is at a location that optimizes the torsional stiffness of the guidewire, the location determined by a Method for Enhancing the Ratio of Torsional Stiffness to Transverse Flexibility as discussed above, or within 15%, 10%, 5%, 2%, 1%, 0.5% or less of the distance between the connection points 22 and 26 from the optimal location.

The core and the sleeve in each of the embodiments discussed above, may include any of a broad variety of structures, configurations, and/or materials, as desired. For example, the core 28 above was depicted as having a solid circular cross section. This is merely an example embodiment and other cross-sections are contemplated, such as oval, rectangular and crescent-shaped. The cross-section may vary along the length as, for example, from a circular cross section to a narrow rectangular ribbon. The core may have one or more smoothly tapering sections, or one or more step-wise transitions, or both. The core may include one or more areas having a ridge, ridges, bumps or knurling as desired to provide a secure or reliable attachment surface for attachments such as adhesives, solders or interference fits. The material may be uniform throughout, as is the case in the embodiment of FIG. 2 or a combination of materials may be used. For example, the core may have a center made of one metal and an outer layer made from another or may have a proximal portion made from one material and a distal portion made from another.

A sleeve suitable for use with an embodiment, such as that of FIG. 10, may also be fashioned with a plurality of slots or cuts to increase its flexibility without substantially reducing its torsional stiffness. In a typical arrangement, a pair or trio of slots is cut into the tube wall in a plane normal to the longitudinal axis of the tube. This arrangement is repeated along the length of the tube, varying the axis position of one set of slots with respect to the next by offsetting it 60 degrees, 85 degrees, 90 degrees or some desired axial offset. The slot pattern, spacing and size can be uniform along the length of the tube to produce a tube of uniform properties along its length or these attributes may be varied. For example, the slot size could increase distally to produce a tube of distally increasing flexibility. Likewise, the slot spacing (the distance from one set of slots to the next) can be decreased distally. The slot pattern may be varied as well, varying between sets of two uniformly spaced slots and sets of three uniformly spaced slots, for example, or changing from a pattern of uniform spacing to a pattern of non-uniform spacing to create a region that has preferential bending characteristics. Of course, regions with different patterns, spacing and size can be created to form regions with desired characteristics of torque and bending, for example.

Another sleeve suitable for use with an embodiment, such as that of FIG. 8, may also be made from a helical coil. Coils may be made from wire having a circular cross-section or a non-circular cross section, and the spacing between coil loops may be varied as desired. For example a coil could be made from a rectangular ribbon whose narrow edge forms the outer edge of the coil and which has a closed spacing such that the loops of the coil touch each other. The sleeve may be embedded in or enclosed by a polymer layer, if desired. Other contemplated configurations include a wire braid or wire mesh. Of course, the sleeve may include sections of various types. For example, one sleeve may have a proximal section having a solid wall, a middle slotted section and a distal coil. Some additional examples of arrangements of tubular bodies having cuts or slots formed therein that may be suitable for the present application are disclosed in U.S. Pat. No. 6,428,489 and in U.S. Pat. No. 6,579,246, both of which are incorporated herein by reference. Also, some additional examples of arrangements of cuts or slots formed in a tubular body for use in a medical device are disclosed in a U.S. patent application Ser. No. 10/375,493 (Pub. No. US 2004 0167437 A1), which is also incorporated herein by reference.

Some examples of metals and metal alloys suitable for use in either the sleeve 30 or core 28, or other components of the device, can include stainless steel, such as 304V, 304L, and 316L stainless steel; nickel-titanium alloy such as a superelastic (i.e. pseudoelastic) or linear elastic or shape-memory nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. In some embodiments, it is desirable to use metals, or metal alloys that are suitable for metal joining techniques such as welding, soldering, brazing, crimping, friction fitting, adhesive bonding, etc. As noted above, the sleeve or core may also be formed of or include polymer materials. Some examples of polymeric materials may include, but are not limited to: poly (L-lactide) (PLLA), poly(D,L-lactide) (PLA), polyglycolide (PGA), poly(L-lactide-co-D,L-lactide) (PLLA/PLA), poly (L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxybutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly (phosphate ester), poly(amino acid), poly(hydroxy butyrate), polyacrylate, polyacrylamid, poly(hydroxyethyl methacrylate), polyurethane, polysiloxane and their copolymers, or mixtures or combinations thereof.

Additional materials and/or configurations for both the sleeve and the core may be found in U.S. patent application Ser. No. 10/400,750 (Pub. No. US 2004 0193140 A1), incorporated herein by reference.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. None of the description in the present application should be read as implying that any particular element, step, or function is an essential element which must be included in the claim scope. Moreover, none of these claims are intended to invoke 35 U.S.C. §112, ¶ 6 unless the exact words "means for" are followed by a participle. The invention's scope is, of course, defined in the language in which the appended claims are expressed.

What is claimed is:

1. An intravascular medical device having a longitudinal axis, the device comprising:

a first elongate member having a first end, a second end, a length, and a lumen disposed between the first and second end;

a second elongate member disposed in the lumen of the first elongate member;

a first connection between the first elongate member and the second elongate member proximate the first end;

a second connection between the first elongate member and the second elongate member proximate the second end, the first and second connections being spaced apart by a distance; and a third connection between the first and second elongate members, wherein the first elongate member has a portion that extends from the first connection to the second connection, the first elongate member portion having a length that extends from the first connection to the second connection, a shear modulus and a polar moment of inertia, wherein the second elongate member has a portion that extends from the first connection to the second connection, the second elongate member portion having a length that extends from the first connection to the second connection, a shear modulus and a polar moment of inertia, wherein the elongate member has a torsional stiffness that is a function of the lengths, shear moduli and polar moments of inertia of the first and second elongate member portions, and wherein the third connection is disposed at a longitudinal position that maximizes the torsional stiffness.

2. The medical device of claim 1 wherein the first elongate member comprises a tube having a plurality of slots defined therein.

3. The medical device of claim 2 wherein the first elongate member comprises a slotted hypotube.

4. The medical device of claim 3 wherein the slots are configured to make at least a portion of the first elongate member more flexible about an axis normal to the longitudinal axis.

5. The medical device of claim 1 wherein the first elongate member comprises a coil.

6. The medical device of claim 5 wherein the coil comprises a flat ribbon.

7. The medical device of claim 5 wherein the coil comprises a first section having a plurality of uniformly spaced turns.

8. The medical device of claim 7 wherein the coil comprises a second section having a plurality of turns having a different spacing from that of the first section.

9. The medical device of claim 5 wherein the coil is imbedded in a tube.

10. The medical device of claim 1 wherein the second elongate member has a first cross-sectional area at a first point and a second cross-sectional area less than the first cross-sectional area at a second point distal to the first point.

11. The medical device of claim 10 wherein the second elongate member comprises a distally tapering section.

12. The medical device of claim 10 wherein the second elongate member comprises a step-wise reduction in cross-section.

13. The medical device of claim 10 wherein the second elongate member has a first length having a constant cross-sectional area along the length, a second length distal to the first length having a distally decreasing cross-sectional area, and a third length distal to the second length having a constant cross-sectional area along the length.

14. The medical device of claim 1 wherein the second elongate member comprises a circular cross-section.

15. The medical device of claim 1 wherein the second elongate member comprises a polygonal cross-section.

16. The medical device of claim 1 wherein the medical device is a guidewire.

17. The medical device of claim 1 further comprising an expandable filter disposed on a distal section thereof.

18. The medical device of claim 1 further comprising a spacer fastened between the first and second elongate members.

19. The medical device of claim 1 further comprising an adhesive between the first and second elongate members.

20. The medical device of claim 1 further comprising a weld between the first and second elongate members.

21. The medical device of claim 1 wherein the first elongate member has a distal end and the second elongate member has a distal end and further comprising a distal tip and wherein the distal ends of the first and second elongate members are embedded therein.

22. The device of claim 1 wherein the first elongate member and the second elongate member are fastened at a second point disposed between the first and the second end, wherein the second point is at a different longitudinal location than the third connection and wherein the third connection and the second point are within 10% of locations that maximize the torsional stiffness.

23. The device of claim 1 further comprising a cavity between the first elongate member and the second elongate member, wherein no more than 10% of the cavity is filled with solid material.

24. The device of claim 1 wherein the third connection is between the first and second elongate member at within 5% of the distance from the optimal torque stiffness location.

25. The device of claim 1 wherein the third connection is between the first and second elongate member at within 2% of the distance from the optimal torque stiffness location.

26. The device of claim 1 wherein the third connection is between the first and second elongate member at within 1% of the distance from the optimal torque stiffness location.

27. An elongate medical device, comprising:
a first elongate member having a proximal end, a distal end and a lumen there between;
a second elongate member having a proximal end and a distal end, the second elongate member at least partially disposed in the first elongate member;
a first connection between first elongate member and the second elongate member proximate the proximal end of the first elongate member;
a second connection between the first elongate member and the second elongate member proximate the distal end of the first elongate member; and
a third connection between the first elongate member and the second elongate member, the third connection disposed between the first and second connections,
wherein the first elongate member has a portion that extends from the first connection to the second connection, the first elongate member portion having a length that extends from the first connection to the second connection, a shear modulus and a polar moment of inertia,
wherein the second elongate member has a portion that extends from the first connection to the second connection, the second elongate member portion having a length that extends from the first connection to the second connection, a shear modulus and a polar moment of inertia,
wherein the elongate member has a torsional stiffness that is a function of the lengths, shear moduli and polar moments of inertia of the first and second elongate member portions, and
wherein the third connection is disposed at a longitudinal position that is within 10% of the first elongate member portion length of a point that maximizes the torsional stiffness.

28. The device of claim 27, wherein the second elongate member includes a section having a continuously changing transverse cross-section.

29. The device of claim 28, wherein the third connection point is located on the section.

30. The device of claim 27, wherein the second elongate member is a core.

31. The device of claim 27, wherein the second elongate member comprises a superelastic material.

32. The device of claim 27, wherein the second elongate member comprises a nickel-titanium alloy.

33. The device of claim 27, wherein the second elongate member has a plurality of cross-sectional areas.

34. The device of claim 33, wherein the cross-sectional area of the second elongate member at the second connection point is less than the cross-sectional area at the first connection point.

35. The device of claim 34, wherein the second elongate member includes a distally tapering region between the first and second connection points.

36. The device of claim 33, wherein the second elongate member includes a first region of uniform cross-sectional area and a second region of uniform cross-sectional area between the two connection points.

37. The device of claim 27, wherein the first elongate member is a metallic tubular member with slots defined therein.

38. The device of claim 27 wherein the first elongate member is a tube having a tube wall and an elongate axis, the tube wall having a plurality of slots disposed therein, the slots being substantially normal to the elongate axis of the tube.

39. The device of claim 38, wherein the slots are disposed in a uniform pattern along a section of the tube.

40. The device of claim 38, wherein the slots are disposed in a pattern of distally increasing density along a section of the tube wall.

41. The device of claim 27, further comprising an expandable filter disposed thereon.

42. The device of claim 27, wherein the third connection is positioned to optimize the torsional rigidity of the elongate medical device between the first and second connections.

43. The device of claim 27, wherein the third connection is disposed at a longitudinal position that is within 5% of the first elongate member portion length of a point that maximizes the torsional stiffness.

44. The device of claim 27, wherein the third connection is disposed at a longitudinal position that is within 2% of the first elongate member portion length of a point that maximizes the torsional stiffness.

45. An elongate medical device, comprising:
a first elongate member having a proximal end, a distal end and a lumen there between;
a second elongate member having a proximal end and a distal end, the second elongate member at least partially disposed in the first elongate member;
a first connection between first elongate member and the second elongate member proximate the proximal end of the first elongate member;
a second connection between the first elongate member and the second elongate member proximate the distal end of the first elongate member; and
a third connection between the first elongate member and the second elongate member, the third connection disposed at a point that maximizes torsional stiffness of the first and second elongate members,
wherein the third connection comprises a collar fixed to the second elongate member at the third connection point and an insert fixed to the first elongate member at the third connection point, the insert defining an open space in which the collar is disposed and through which the collar may move longitudinally but in which the collar is restrained from rotating about a longitudinal axis relative to the insert.

46. The device of claim 45 wherein the collar has an elliptical cross-sectional periphery and the insert has a corresponding elliptical lumen.

* * * * *